(12) United States Patent
Maxik et al.

(10) Patent No.: US 9,174,067 B2
(45) Date of Patent: Nov. 3, 2015

(54) SYSTEM FOR TREATING LIGHT TREATABLE CONDITIONS AND ASSOCIATED METHODS

(71) Applicant: BIOLOGICAL ILLUMINATION, LLC, Satellite Beach, FL (US)

(72) Inventors: Fredric S. Maxik, Indialantic, FL (US); Robert R. Soler, Cocoa Beach, FL (US); Matthew Regan, Melbourne, FL (US)

(73) Assignee: Biological Illumination, LLC, Melbourne, FL (US)

( * ) Notice: Subject to any disclaimer, the term of this patent is extended or adjusted under 35 U.S.C. 154(b) by 162 days.

(21) Appl. No.: 13/832,459

(22) Filed: Mar. 15, 2013

(65) Prior Publication Data
US 2014/0107735 A1    Apr. 17, 2014

Related U.S. Application Data

(63) Continuation-in-part of application No. 13/652,207, filed on Oct. 15, 2012, now Pat. No. 8,643,276.

(51) Int. Cl.
*A61N 5/06* (2006.01)
*A61M 21/02* (2006.01)
*A61M 21/00* (2006.01)

(52) U.S. Cl.
CPC .............. *A61N 5/06* (2013.01); *A61M 21/02* (2013.01); *A61N 5/0618* (2013.01); *A61M 2021/0044* (2013.01); *A61M 2205/3306* (2013.01); *A61M 2230/14* (2013.01); *A61M 2230/16* (2013.01)

(58) Field of Classification Search
CPC ........... A61N 5/05; A61N 5/06; A61N 5/037; A61N 1/371; C12Q 3/00; C12Q 1/527; G01N 21/64
USPC ............ 607/88, 77, 28–29, 35, 59, 62; 435/4; 250/461.1, 461.2
See application file for complete search history.

(56) References Cited

U.S. PATENT DOCUMENTS 4,691,341 A    9/1987  Knoble
5,046,494 A    9/1991  Searfoss et al.
(Continued)

FOREIGN PATENT DOCUMENTS

CN    101702421 A    5/2010
EP    0851260        7/1998
(Continued)

OTHER PUBLICATIONS

U.S. Appl. No. 13/652,207, filed Oct. 2012, Fredric S. Maxik et al.
(Continued)

*Primary Examiner* — Minh D A
(74) *Attorney, Agent, or Firm* — Mark Malek; Daniel Pierron; Widerman Malek, PL

(57) ABSTRACT

A system for treating a light treatable condition may include a luminaire configured to emit diagnostic output spectra and a sensor configured to measure a biotic response to the diagnostic output spectra. A computer may be positioned in electrical communication with each of the luminaire and the sensor and may utilize a measured biotic response to determine prescribed output spectra that is responsive to treat the light treatable condition. The luminaire may also be configurable to emit the prescribed output spectra by receiving an instruction from the computer.

20 Claims, 5 Drawing Sheets

(56) References Cited

U.S. PATENT DOCUMENTS

| | | |
|---|---|---|
| 5,189,412 A | 2/1993 | Mehta |
| 5,319,301 A | 6/1994 | Callahan et al. |
| 5,345,143 A | 9/1994 | Little |
| 5,523,878 A | 6/1996 | Wallace et al. |
| 5,563,422 A | 10/1996 | Nakamura et al. |
| 5,680,230 A | 10/1997 | Kaburagi et al. |
| 5,704,701 A | 1/1998 | Kavanagh et al. |
| 5,813,753 A | 9/1998 | Vriens et al. |
| 5,936,599 A | 8/1999 | Reymond |
| 5,997,150 A | 12/1999 | Anderson |
| 6,028,396 A | 2/2000 | Morrissey, Jr. |
| 6,140,646 A | 10/2000 | Busta et al. |
| 6,259,572 B1 | 7/2001 | Meyer, Jr. |
| 6,341,876 B1 | 1/2002 | Moss et al. |
| 6,356,700 B1 | 3/2002 | Strobl |
| 6,450,652 B1 | 9/2002 | Karpen |
| 6,459,919 B1 | 10/2002 | Lys et al. |
| 6,528,954 B1 | 3/2003 | Lys et al. |
| 6,561,656 B1 | 5/2003 | Kojima et al. |
| 6,577,080 B2 | 6/2003 | Lys et al. |
| 6,586,882 B1 | 7/2003 | Harbers |
| 6,594,090 B2 | 7/2003 | Kruschwitz et al. |
| 6,733,135 B2 | 5/2004 | Dho |
| 6,734,639 B2 | 5/2004 | Chang et al. |
| 6,762,562 B2 | 7/2004 | Leong |
| 6,767,111 B1 | 7/2004 | Lai |
| 6,798,154 B1 | 9/2004 | Sullivan et al. |
| 6,817,735 B2 | 11/2004 | Shimizu et al. |
| 6,853,150 B2 | 2/2005 | Clauberg et al. |
| 6,870,523 B1 | 3/2005 | Ben-David et al. |
| 6,871,982 B2 | 3/2005 | Holman et al. |
| 6,876,007 B2 | 4/2005 | Yamazaki et al. |
| 6,902,296 B2 | 6/2005 | Searfoss, III |
| 6,949,894 B1 | 9/2005 | Sullivan et al. |
| 6,965,205 B2 | 11/2005 | Piepgras |
| 6,967,761 B2 | 11/2005 | Starkweather et al. |
| 6,974,713 B2 | 12/2005 | Patel et al. |
| 7,008,559 B2 | 3/2006 | Chen |
| 7,014,336 B1 | 3/2006 | Ducharme et al. |
| 7,034,934 B2 | 4/2006 | Manning |
| 7,042,623 B1 | 5/2006 | Huibers et al. |
| 7,055,994 B2 | 6/2006 | Martin |
| 7,058,197 B1 | 6/2006 | McGuire et al. |
| 7,066,628 B2 | 6/2006 | Allen |
| 7,070,281 B2 | 7/2006 | Kato |
| 7,072,096 B2 | 7/2006 | Holman et al. |
| 7,075,707 B1 | 7/2006 | Rapaport et al. |
| 7,083,304 B2 | 8/2006 | Rhoads |
| 7,095,053 B2 | 8/2006 | Mazzochette et al. |
| 7,112,806 B2 * | 9/2006 | Lussier .................. 250/458.1 |
| 7,138,770 B2 | 11/2006 | Uang et al. |
| 7,144,131 B2 | 12/2006 | Rains |
| 7,157,745 B2 | 1/2007 | Blonder et al. |
| 7,161,313 B2 | 1/2007 | Piepgras |
| 7,178,941 B2 | 2/2007 | Roberge et al. |
| 7,184,201 B2 | 2/2007 | Duncan |
| 7,187,484 B2 | 3/2007 | Mehrl |
| 7,213,926 B2 | 5/2007 | May et al. |
| 7,234,844 B2 | 6/2007 | Bolta et al. |
| 7,246,923 B2 | 7/2007 | Conner |
| 7,247,874 B2 | 7/2007 | Bode et al. |
| 7,252,408 B2 | 8/2007 | Mazzochete et al. |
| 7,255,469 B2 | 8/2007 | Wheatley et al. |
| 7,261,453 B2 | 8/2007 | Morejon et al. |
| 7,289,090 B2 | 10/2007 | Morgan |
| 7,300,177 B2 | 11/2007 | Conner |
| 7,303,291 B2 | 12/2007 | Ikeda et al. |
| 7,319,293 B2 | 1/2008 | Maxik |
| 7,324,076 B2 | 1/2008 | Lee et al. |
| 7,325,956 B2 | 2/2008 | Morejon et al. |
| 7,342,658 B2 | 3/2008 | Kowarz et al. |
| 7,344,279 B2 | 3/2008 | Mueller et al. |
| 7,349,095 B2 | 3/2008 | Kurosaki |
| 7,353,859 B2 | 4/2008 | Stevanovic et al. |
| 7,369,056 B2 | 5/2008 | McCollough et al. |
| 7,382,091 B2 | 6/2008 | Chen |
| 7,382,632 B2 | 6/2008 | Alo et al. |
| 7,400,439 B2 | 7/2008 | Holman |
| 7,427,146 B2 | 9/2008 | Conner |
| 7,429,983 B2 | 9/2008 | Islam |
| 7,434,946 B2 | 10/2008 | Huibers |
| 7,436,996 B2 | 10/2008 | Ben-Chorin |
| 7,438,443 B2 | 10/2008 | Tatsuno et al. |
| 7,455,435 B2 | 11/2008 | Mathews |
| 7,476,016 B2 | 1/2009 | Kurihara |
| 7,489,086 B2 | 2/2009 | Miskin et al. |
| 7,497,596 B2 | 3/2009 | Ge |
| 7,520,607 B2 | 4/2009 | Casper et al. |
| 7,520,642 B2 | 4/2009 | Holman et al. |
| 7,521,875 B2 | 4/2009 | Maxik |
| 7,528,421 B2 | 5/2009 | Mazzochete |
| 7,530,708 B2 | 5/2009 | Park |
| 7,537,347 B2 | 5/2009 | Dewald |
| 7,540,616 B2 | 6/2009 | Conner |
| 7,556,376 B2 | 7/2009 | Ishak et al. |
| 7,556,406 B2 | 7/2009 | Petroski et al. |
| 7,567,040 B2 | 7/2009 | Pong et al. |
| 7,573,210 B2 | 8/2009 | Ashdown et al. |
| 7,598,682 B2 | 10/2009 | Grajcar |
| 7,598,686 B2 | 10/2009 | Lys et al. |
| 7,598,961 B2 | 10/2009 | Higgins |
| 7,605,971 B2 | 10/2009 | Ishii et al. |
| 7,619,372 B2 | 11/2009 | Garrity |
| 7,626,755 B2 | 12/2009 | Furuya et al. |
| 7,633,093 B2 | 12/2009 | Blonder et al. |
| 7,633,779 B2 | 12/2009 | Garrity et al. |
| 7,637,643 B2 | 12/2009 | Maxik |
| 7,677,736 B2 | 3/2010 | Kasazumi et al. |
| 7,678,140 B2 | 3/2010 | Brainard et al. |
| 7,679,281 B2 | 3/2010 | Kim et al. |
| 7,684,007 B2 | 3/2010 | Hull et al. |
| 7,703,943 B2 | 4/2010 | Li et al. |
| 7,705,810 B2 | 4/2010 | Choi et al. |
| 7,708,452 B2 | 5/2010 | Maxik et al. |
| 7,709,811 B2 | 5/2010 | Conner |
| 7,719,766 B2 | 5/2010 | Grasser et al. |
| 7,728,846 B2 | 6/2010 | Higgins et al. |
| 7,732,825 B2 | 6/2010 | Kim et al. |
| 7,748,845 B2 | 7/2010 | Casper et al. |
| 7,766,490 B2 | 8/2010 | Harbers et al. |
| 7,819,556 B2 | 10/2010 | Heffington et al. |
| 7,828,453 B2 | 11/2010 | Tran et al. |
| 7,828,465 B2 | 11/2010 | Roberge et al. |
| 7,832,878 B2 | 11/2010 | Brukilacchio et al. |
| 7,834,867 B2 | 11/2010 | Sprague et al. |
| 7,835,056 B2 | 11/2010 | Doucet et al. |
| 7,841,714 B2 | 11/2010 | Grueber |
| 7,845,823 B2 | 12/2010 | Mueller et al. |
| 7,852,017 B1 | 12/2010 | Melanson |
| 7,855,376 B2 | 12/2010 | Cantin et al. |
| 7,871,839 B2 | 1/2011 | Lee |
| 7,880,400 B2 | 2/2011 | Zhoo et al. |
| 7,889,430 B2 | 2/2011 | El-Ghoroury et al. |
| 7,906,789 B2 | 3/2011 | Jung et al. |
| 7,928,565 B2 | 4/2011 | Brunschwiler et al. |
| 7,972,030 B2 | 7/2011 | Li |
| 7,976,182 B2 | 7/2011 | Ribarich |
| 7,976,205 B2 | 7/2011 | Grotsch et al. |
| 7,984,989 B2 | 7/2011 | Gruber |
| 8,013,545 B2 | 9/2011 | Jonsson |
| 8,016,443 B2 | 9/2011 | Falicoff et al. |
| 8,040,070 B2 | 10/2011 | Myers et al. |
| 8,047,660 B2 | 11/2011 | Penn et al. |
| 8,049,763 B2 | 11/2011 | Kwak et al. |
| 8,061,857 B2 | 11/2011 | Liu et al. |
| 8,070,302 B2 | 12/2011 | Hatanaka et al. |
| 8,076,680 B2 | 12/2011 | Lee et al. |
| 8,083,364 B2 | 12/2011 | Allen |
| 8,096,668 B2 | 1/2012 | Abu-Ageel |
| 8,115,419 B2 | 2/2012 | Given et al. |
| 8,164,844 B2 | 4/2012 | Toda et al. |
| 8,182,106 B2 | 5/2012 | Shin |
| 8,182,115 B2 | 5/2012 | Takahashi et al. |
| 8,188,687 B2 | 5/2012 | Lee et al. |

(56) References Cited

U.S. PATENT DOCUMENTS

| | | | |
|---|---|---|---|
| 8,192,047 B2 | 6/2012 | Bailey et al. |
| 8,207,676 B2 | 6/2012 | Hilgers |
| 8,212,836 B2 | 7/2012 | Matsumoto et al. |
| 8,253,336 B2 | 8/2012 | Maxik et al. |
| 8,256,921 B2 | 9/2012 | Crookham et al. |
| 8,274,089 B2 | 9/2012 | Lee |
| 8,297,783 B2 | 10/2012 | Kim |
| 8,304,978 B2 | 11/2012 | Kim et al. |
| 8,310,171 B2 | 11/2012 | Reisenauer et al. |
| 8,319,445 B2 | 11/2012 | McKinney et al. |
| 8,324,808 B2 | 12/2012 | Maxik et al. |
| 8,324,823 B2 | 12/2012 | Choi et al. |
| 8,324,840 B2 | 12/2012 | Shteynberg et al. |
| 8,331,099 B2 | 12/2012 | Geissler et al. |
| 8,337,029 B2 | 12/2012 | Li |
| 8,378,574 B2 | 2/2013 | Schlangen et al. |
| 8,384,984 B2 | 2/2013 | Maxik et al. |
| 8,401,231 B2 | 3/2013 | Maxik et al. |
| 8,405,299 B2 | 3/2013 | Toda et al. |
| 8,410,717 B2 | 4/2013 | Shteynberg |
| 8,410,725 B2 | 4/2013 | Jacobs |
| 8,446,095 B2 | 5/2013 | Maxik et al. |
| 8,643,276 B2 * | 2/2014 | Maxik et al. ............ 315/32 |
| 2002/0113555 A1 | 8/2002 | Lys et al. |
| 2004/0052076 A1 | 3/2004 | Mueller et al. |
| 2004/0093045 A1 | 5/2004 | Bolta |
| 2004/0119086 A1 | 6/2004 | Yano et al. |
| 2005/0189557 A1 | 9/2005 | Mazzochette et al. |
| 2005/0218780 A1 | 10/2005 | Chen |
| 2005/0267213 A1 | 12/2005 | Gold et al. |
| 2006/0002108 A1 | 1/2006 | Ouderkirk et al. |
| 2006/0002110 A1 | 1/2006 | Dowling et al. |
| 2006/0085301 A1 | 4/2006 | Leahy |
| 2006/0164005 A1 | 7/2006 | Sun |
| 2006/0232992 A1 | 10/2006 | Bertram et al. |
| 2006/0285193 A1 | 12/2006 | Kimura et al. |
| 2007/0013871 A1 | 1/2007 | Marshall et al. |
| 2007/0159492 A1 | 7/2007 | Lo et al. |
| 2007/0165193 A1 | 7/2007 | Kubo et al. |
| 2007/0188847 A1 | 8/2007 | McDonald et al. |
| 2007/0241340 A1 | 10/2007 | Pan |
| 2007/0262714 A1 | 11/2007 | Bylsma |
| 2008/0119912 A1 | 5/2008 | Hayes |
| 2008/0143973 A1 | 6/2008 | Wu |
| 2008/0198572 A1 | 8/2008 | Medendorp |
| 2008/0232084 A1 | 9/2008 | Kon |
| 2008/0258643 A1 | 10/2008 | Cheng et al. |
| 2009/0009102 A1 | 1/2009 | Kahlman et al. |
| 2009/0059099 A1 | 3/2009 | Linkov et al. |
| 2009/0059585 A1 | 3/2009 | Chen et al. |
| 2009/0128781 A1 | 5/2009 | Li |
| 2009/0160370 A1 | 6/2009 | Tai et al. |
| 2009/0231088 A1 | 9/2009 | Famik |
| 2009/0232683 A1 | 9/2009 | Hirata et al. |
| 2009/0273931 A1 | 11/2009 | Ito et al. |
| 2009/0303694 A1 | 12/2009 | Roth et al. |
| 2010/0001652 A1 | 1/2010 | Damsleth |
| 2010/0006762 A1 | 1/2010 | Yoshida et al. |
| 2010/0051976 A1 | 3/2010 | Rooymans |
| 2010/0053959 A1 | 3/2010 | Ijzerman et al. |
| 2010/0076250 A1 | 3/2010 | Van Woudenberg |
| 2010/0103389 A1 | 4/2010 | McVea et al. |
| 2010/0111369 A1 * | 5/2010 | Lussier ............ 382/110 |
| 2010/0121420 A1 | 5/2010 | Fiset et al. |
| 2010/0157573 A1 | 6/2010 | Toda et al. |
| 2010/0202129 A1 | 8/2010 | Abu-Ageel |
| 2010/0213859 A1 | 8/2010 | Shteynberg et al. |
| 2010/0231131 A1 | 9/2010 | Anderson |
| 2010/0231863 A1 | 9/2010 | Hikmet et al. |
| 2010/0244700 A1 | 9/2010 | Chong et al. |
| 2010/0244724 A1 | 9/2010 | Jacobs et al. |
| 2010/0244735 A1 | 9/2010 | Buelow, II |
| 2010/0244740 A1 | 9/2010 | Alpert et al. |
| 2010/0270942 A1 | 10/2010 | Hui et al. |
| 2010/0277084 A1 | 11/2010 | Lee et al. |
| 2010/0277316 A1 | 11/2010 | Schlangen et al. |
| 2010/0302464 A1 | 12/2010 | Raring et al. |
| 2010/0308738 A1 | 12/2010 | Shteynberg et al. |
| 2010/0315320 A1 | 12/2010 | Yoshida |
| 2010/0320927 A1 | 12/2010 | Gray et al. |
| 2010/0320928 A1 | 12/2010 | Kaihotsu et al. |
| 2010/0321641 A1 | 12/2010 | Van Der Lubbe |
| 2011/0012137 A1 | 1/2011 | Lin et al. |
| 2011/0057786 A1 | 3/2011 | Giddens |
| 2011/0062888 A1 | 3/2011 | Bondy |
| 2011/0080635 A1 | 4/2011 | Takeuchi |
| 2011/0299277 A1 | 12/2011 | Ehara |
| 2011/0310446 A1 | 12/2011 | Komatsu |
| 2012/0008326 A1 | 1/2012 | Jou |
| 2012/0285667 A1 | 11/2012 | Maxik et al. |
| 2012/0286673 A1 | 11/2012 | Holland et al. |
| 2012/0286700 A1 | 11/2012 | Maxik et al. |
| 2013/0070439 A1 | 3/2013 | Maxik et al. |
| 2013/0140988 A1 | 6/2013 | Maxik et al. |

FOREIGN PATENT DOCUMENTS

| | | |
|---|---|---|
| EP | 1671059 B1 | 4/2007 |
| EP | 2 199 657 | 6/2010 |
| EP | 2 242 335 | 10/2010 |
| EP | 2292464 A1 | 9/2011 |
| JP | 2008226567 | 9/2008 |
| WO | WO03098977 | 11/2003 |
| WO | WO2004011846 A1 | 2/2004 |
| WO | WO2006001221 A1 | 1/2006 |
| WO | WO2009121539 A1 | 10/2009 |
| WO | WO 2010027459 | 3/2010 |
| WO | WO 2010098811 | 9/2010 |
| WO | WO 2011008251 | 1/2011 |
| WO | WO 2011016860 | 2/2011 |
| WO | WO 2012012245 A2 | 1/2012 |
| WO | WO 2012064470 | 5/2012 |
| WO | WO 2012135173 | 10/2012 |
| WO | WO 2012158665 | 11/2012 |
| WO | PCTUS2012067916 | 12/2012 |

OTHER PUBLICATIONS

U.S. Appl. No. 13/709,942, filed Dec. 2012, Fredric S. Maxik et al.
U.S. Appl. No. 13/715,085, filed Dec. 2012, Fredric S. Maxik et al.
U.S. Appl. No. 13/737,606, filed Jan. 2013, Fredric S. Maxik et al.
U.S. Appl. No. 13/739,665, filed Jan. 2013, Fredric S. Maxik et al.
U.S. Appl. No. 13/751,180, filed Jan. 2013, Fredric S. Maxik et al.
U.S. Appl. No. 13/753,890, filed Jan. 2013, Fredric S. Maxik et al.
U.S. Appl. No. 13/775,936, filed Feb. 2013, Fredric S. Maxik et al.
U.S. Appl. No. 13/792,354, filed Mar. 2013, Fredric S. Maxik et al.
U.S. Appl. No. 13/803,825, filed Mar. 2013, Fredric S. Maxik et al.
U.S. Appl. No. 13/832,459, filed Mar. 2013, Fredric S. Maxik et al.
U.S. Appl. No. 13/837,643, filed Mar. 2013, Fredric S. Maxik et al.
U.S. Appl. No. 13/842,875, filed Mar. 2013, Eric Holland et al.
4Sevens.com, Futlight Color Temperature Adjustable Light Panel, 600x600, www.4sevens.com/product_info.php?products_id=2673, (2012).
Akashi, Yukio, et al., Assessment of Headlamp Glare and Potential Countermeasures: Survey of Advanced Front Lighting System (AFS), U.S. Department of Transportation, National Highway Traffic Safety Administration, Contract No. DTNH22-99-D-07005, (Dec. 2005).
Arthur P. Fraas, Heat Exchanger Design, 1989, p. 60, John Wiley & Sons, Inc., Canada.
Binnie et al. (1979) "Fluorescent Lighting and Epilepsy" Epilepsia 20(6):725-727.
Boeing, (Jul. 6, 2011), International Space Program, S684-13489 Revision A "ISS Interior Solid State Lighting Assembly (SSLA) Specification", Submitted to National Aeronautics and Space Administration, Johnson Space Center, Contract No. NAS15-10000, pp. 1-60.
Brainard, et al., (Aug. 15, 2001), "Action Spectrum for Melatonin Regulation in Humans: Evidence for a Novel Circadian Photoreceptor", The Journal of Neuroscience, 21(16):6405-6412.

(56) References Cited

OTHER PUBLICATIONS

Bullough, John, et al., "Discomfort Glare from Headlamps: Interactions Among Spectrum, Control of Gaze and Background Light Level", Society of Automotive Engineers, Inc., 2003-01-0296, (2003).
Charamisinau et al. (2005) "Semiconductor laser insert with Uniform Illumination for Use in Photodynamic Therapy" Appl Opt 44(24):5055-5068.
Derlofske, et al., "Headlamp Parameters and Glare", Society of Automotive Engineers, Inc., 2004-01-1280, (2004).
ERBA Shedding Light on Photosensitivity, One of Epilepsy's Most Complex Conditions. Photosensitivity and Epilepsy. Epilepsy Foundation. Accessed: Aug. 28, 2009. http://www.epilepsyfoundation.org/aboutepilepsy/seizures/photosensitivity-/gerba.cfm.
Figueiro et al. (2004) "Spectral Sensitivity of the Circadian System" Proc. SPIE 5187:207.
Figueiro et al. (2008) "Retinal Mechanisms Determine the Subadditive Response to Polychromatic Light by the Human Circadian System" Neurosci Lett 438(2):242.
Gabrecht et al. (2007) "Design of a Light Delivery System for the Photodynamic Treatment of the Crohn's Disease" Proc. SPIE 6632:1-9.
H. A El-Shaikh, S. V. Garimella, "Enhancement of Air Jet Impingement Heat Transfer using Pin-Fin Heat Sinks", D IEEE Transactions on Components and Packaging Technology, Jun. 2000, vol. 23, No. 2.
Happawana et al. (2009) "Direct De-Ionized Water-Cooled Semiconductor Laser Package for Photodynamic Therapy of Esophageal Carcinoma: Design and Analysis" J Electron Pack 131(2):1-7.
Harding & Harding (1999) "Televised Material and Photosensitive Epilepsy" Epilepsia 40(Suppl. 4):65.
Hickcox, Sweater K., et al., Lighting Research Center, "Effect of different colored background lighting on LED discomfort glare perception", Proc. of SPIE, vol. 8484, 84840O-1, (2012).
Jones, Eric D., Light Emitting Diodes (LEDS) for General Lumination, an Optoelectronics Industry Development association (OIDA) Technology Roadmap, OIDA Report, Mar. 2001, published by OIDA in Washington D.C.
J. Y. San, C. H. Huang, M. H, Shu, "Impingement cooling of a confined circular air jet", In t. J. Heat Mass Transf., 1997. pp. 1355-1364, vol. 40.
Kooi, Frank, "Yellow Lessens Discomfort Glare: Physiological Mechanism(S)", TNO Human Factors, Netherlands, Contract No. FA8655-03-1-3043, (Mar. 9, 2004).
Kuller & Laike (1998) "The Impact of Flicker from Fluorescent Lighting on Well-Being, Perfiormance and Physiological Arousal" Ergonomics 41(4):433-447.
Lakatos (2006) "Recent trends in the epidemiology of Inflammatory Bowel Disease: Up or Down?" World J Gastroenterol 12(38):6102.

Mace, Douglas, et al., "Countermeasures for Reducing the Effects of Headlight Glare", The Last Resource, Prepared for the AAA Foundation for Traffic Safety, pp. 1 to 110, (Dec. 2001).
Mehta, Arpit, "Map Colors of a CIE Plot and Color Temperature Using an RGB Color Sensor", Strategic Applications Engineer, Maxim Integrated Products, A1026, p. 1-11, (2005).
N. T. Obot, W. J. Douglas, A S. Mujumdar, "'Effect of Semi-confinement on Impingement Heat Transfer", Proc. 7th Int. Heat Transf. Conf., 1982, pp. 1355-1364. vol. 3.
Ortner & Dorta (2006) "Technology Insight: Photodynamic Therapy for Cholangiocarcinoma" Nat Clin Pract Gastroenterol Hepatol 3(8):459-467.
Rea (2010) "Circadian Light" J Circadian Rhythms 8(1):2.
Rea et al. (2010) "The Potential of Outdoor Lighting for Stimulating the Human Circadian System" Alliance for Solid-State Illumination Systems and Technologies (ASSIST), May 13, 2010, p. 1-11.
Rosco Laboratories Poster "Color Filter Technical Data Sheet: #87 Pale Yellow Green" (2001).
Shenzhen Wei Zing Xin Electronic Technology Co., ltd., Hot Color Temperature Adjustable Led Bulb Light, Alibaba.com, www.alibaba.com/product-gs/616428577/Hot_color_tempature_adjustable_led_bulb.html, (Oct. 4, 2012).
Sivak, Michael, et al., "Blue Content of LED Headlamps and Discomfort Glare", The University of Michigan Transportation Research Institute, Report No. UMTRI-2005-2, pp. 1-18, (Feb. 2005).
S. A Solovitz, L. D. Stevanovic, R. A Beaupre, "Microchannels Take Heatsinks to the Next Level", Power Electronics Technology, Nov. 2006.
Stevens (1987) "Electronic Power Use and Breast Cancer: A Hypothesis" Am J Epidemiol 125(4):556-561.
Stockman, Andrew, "The spectral sensitivity of the human short-wavelength sensitive cones derived from thresholds and color matches", Pergamon, Vision Research 39, pp. 2901-2927 (1999).
Tannith Cattermole, "Smart Energy Class controls light on demand", Gizmag.com, Apr. 18, 2010 accessed Nov. 1, 2011.
Topalkara et al. (1998) "Effects of flash frequency and repetition of intermittent photic stimulation on photoparoxysmal responses" Seizure 7(13):249-253.
Veitch & McColl (1995) "Modulation of Fluorescent Light: Flicker Rate and Light Source Effects on Visual Performance and Visual Comfort" Lighting Research and Technology 27:243-256.
Wang (2005) "The Critical Role of Light in Promoting Intestinal Inflammation and Crohn's Disease" J Immunol 174 (12):8173-8182.
Wilkins et al. (1979) "Neurophysical aspects of pattern-sensitive epilepsy" Brain 102:1-25.
Wilkins et al. (1989) "Fluorescent lighting, headaches, and eyestrain" Lighting Res Technol 21(1):11-18.
Yongmann M. Chung, Kai H. Luo, "Unsteady Heat Transfer Analysis of an Impinging Jet", Journal of Heat Transfer—Transactions of the ASME, Dec. 2002, pp. 1039-1048, vol. 124, No. 6.

* cited by examiner

SYSTEM FOR TREATING LIGHT TREATABLE CONDITIONS AND ASSOCIATED METHODS

RELATED APPLICATIONS

This application is a continuation-in-part of U.S. patent application Ser. No. 13/652,207 filed Oct. 15, 2012, entitled LED LAMP FOR PRODUCING BIOLOGICALLY-CORRECTED LIGHT, and is related to U.S. patent application Ser. No. 13/751,180 filed Jan. 28, 2013, entitled PROGRAMMABLE LUMINAIRE SYSTEM, the entire contents of each of which are incorporated herein by reference.

FIELD OF THE INVENTION

The present invention relates to systems and methods for generating light. More specifically, the present invention relates to a lighting system and method for emitting light to treat light treatable conditions.

BACKGROUND

It is known that a person's physiology and wellbeing can be influenced by phototherapy. The light entering the eye of a person may impact the production of melatonin, which increases during darkness, and can be reduced by the influence of light. Phototherapy may be also used to treat conditions such as acne, skin cancer, psoriasis, seasonal affective disorder and to advance or delay circadian rhythms. Light can also be tailored to positively or negatively enhance the presence of certain colors by altering the wavelength of the emitted light. Individuals that suffer from color blindness may prefer to have the light tailored to their particular visual abilities.

A phototherapy device is disclosed, for example, in U.S. Patent Application Publication No. 2012/0316623 by Ii, et al. The Ii et al. reference discloses a phototherapy device that can irradiate an affected part of a patient's body. U.S. Patent Application Publication No. 2006/0167532 by Parker discloses a phototherapy treatment device for applying area lighting to a wound. U.S. Pat. No. 8,069,857 by Chung et al. discloses a phototherapy method. The Chung et al. reference discloses a method of providing phototherapy to a patient.

These devices utilize phototherapy but they do not tailor the light treatment to an individual, based upon the viewing characteristics and abilities of the individual. Therefore, a need exists to enable a luminaire to produce light that is tailored to an individual's specific vision abilities and treat light treatable conditions.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

Provided herein are systems and methods that address the above-identified problems. More specifically, the present invention advantageously provides a method and system for treating a light treatable condition. The system may enable a luminaire to be tailored to emit light of particular wavelengths where the wavelengths selected for emission may be selected based upon a diagnosis or may also be selected based upon the user's requests and preferences. Furthermore, the tailoring of the luminaire's light production enables a user to have a more enjoyable visual experience by enhancing the colors that the user would find most pleasing.

These and other features, benefits and advantages are provided by a system for treating a light treatable condition that include a luminaire which may be configured to emit diagnostic output spectra and a sensor which may be configured to measure a biotic response to the diagnostic output spectra to define a measured biotic response. The system may also include a computer in electrical communication with the luminaire and the sensor which may utilize the measured biotic response to determine a prescribed output spectra that is responsive to treat the light treatable condition. The luminaire may be configurable to emit the prescribed output spectra by receiving an instruction from the computer.

The measured biotic response may be a retinal response, an eye spectral response and/or a measurement of the pupillary light reflex. In an embodiment of the system, the prescribed output spectra may be based, at least in part, on the visual acuity of a patient. In another embodiment, a computer may be configured so that the prescribed output spectra for the patient is based on a visual acuity of the patient, the measured biotic response, and/or the patient's light preferences.

The prescribed output spectra may be transmittable to a patient device. The system may also include a second luminaire that is configurable to emit the prescribed output spectra based on receipt of instructions from the computer. The prescribed output spectra may also be responsive to a task performed by a patient and/or the time of day during which the patient will observe the prescribed output spectrum. In an embodiment of the system where the prescribed output spectra is responsive to the time of day during which the patient may observe the prescribed output spectra, the luminaire may comprise an autonomous clock configured to cause the luminaire to emit the prescribed output spectra at an indicated time of the day.

A method aspect for the present invention may be for treating a condition in a patient having a light treatable condition. The method may include exposing the patient to diagnostic output spectra and determining the patient's response to the diagnostic output spectra to define a measured patient's response. The method may also include determining a diagnosis of the patient based, at least in part, on the patient's response to the diagnostic output spectra. The method may further include determining a prescribed output spectra that is responsive to the diagnosis, and configuring a luminaire to emit the prescribed output spectra.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use an LED lighting system in accordance with the present invention. In the drawings, like reference numbers indicate identical or functionally similar elements.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art will realize that the following embodiments of the present invention are only illustrative and are not intended to be limiting in any way. Other embodiments of the present invention will readily suggest themselves to such skilled persons having the benefit of this disclosure. Like numbers refer to like elements throughout.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
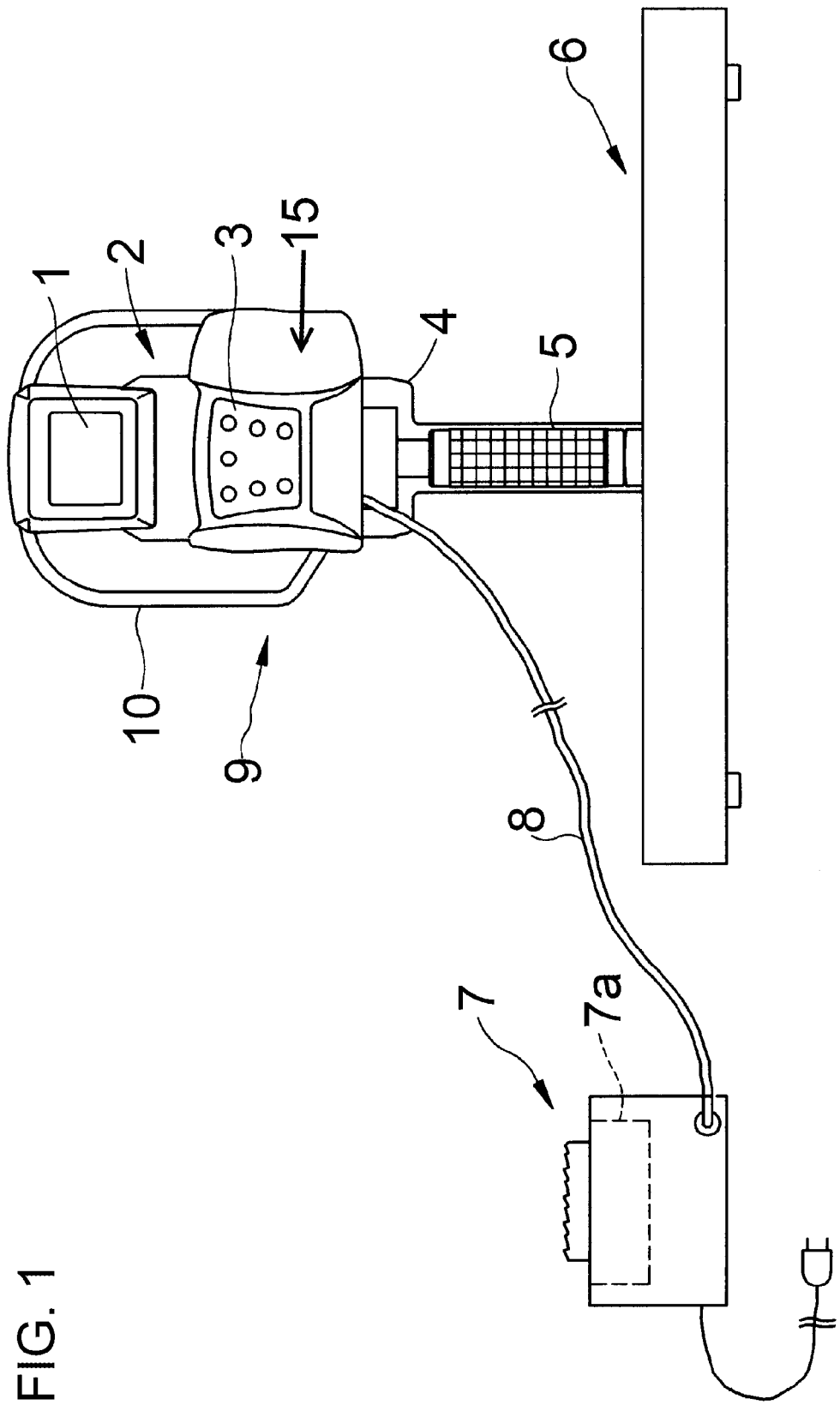
FIG. 1 is a front view of a system for treating a light treatable condition according to an embodiment of the present invention.
Figure 2:
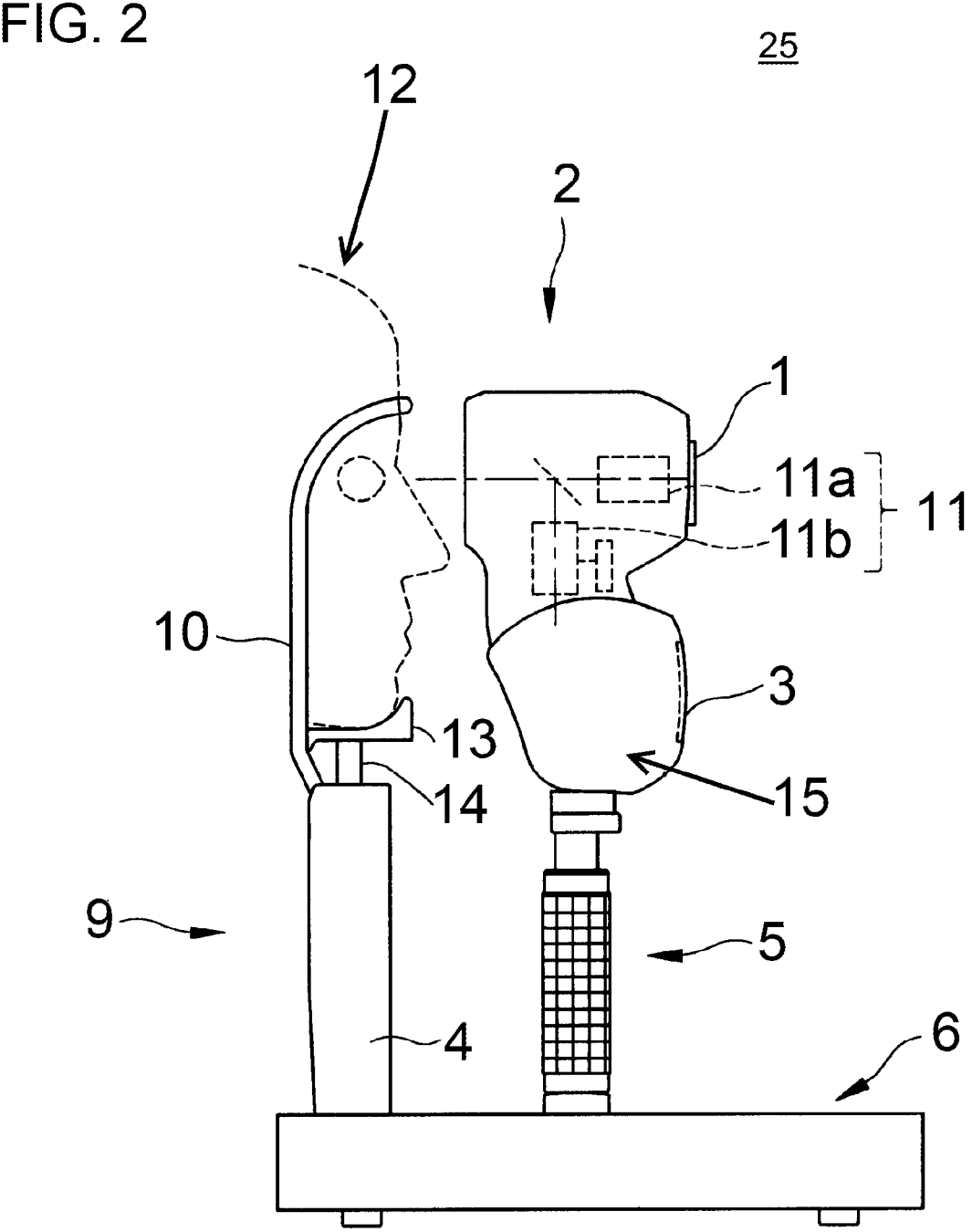
FIG. 2 is a side view of the eye analysis system of FIG. 1.

Referring now to FIGS. 1-2, a system 25 for treating a light treatable condition is disclosed. The system 25 may include an eye analysis system 2 for analyzing a person's eye. An LCD monitor 1 may display the results of the analysis. The system 25 may be operated by the control panel or user interface 3. The control panel or user interface 3 is illustrated as being connected to a portion of the eye analysis system 2, but those skilled in the art will appreciate that the control panel or user interface 3 may be a separate device that is in communication with the eye analysis system 2. The computer 15 may be operated by entering commands via the control panel 3. Similarly, the computer 15 may also be separated from the eye analysis system 2, and positioned in communication with the eye analysis system and the controller or user interface 3. The eye analysis system 2 of the system 25 for treating a light treatable condition may also include a support base 4 and an adjustable vertical stand 5. The entire eye analysis system 2 may be mounted on the base 6.

The system 25 for treating a light treatable condition may include a luminaire programming station 7, which may be utilized to program a luminaire to emit a light suitable for treating a light treatable condition. More particularly, a luminaire may be placed inside the luminaire programming station 7 where it may receive its instructions from the computer 15 via wired connection 8. More information regarding the programming of the luminaire may be found in U.S. patent application Ser. No. 13/751,180, which is incorporated hereinabove.

Another embodiment of the invention may enable the computer to communicate with the luminaire programming station 7 via a wireless connection. The head support unit 9 and forehead rest 10 may enable a patient or user to comfortably place their head in position for an eye examination. Accordingly, those skilled in the art will appreciate that the present invention contemplates that data and/or instructions to program a luminaire to emit a light suitable for treating a light treatable condition may be transmitted to the luminaire wirelessly. This is possible when using a luminaire adapted to receive data wirelessly and, more specifically, programming data.

The programming data may, for example, be directed to a wavelength of the light to be emitted from the luminaire to treat the light treatable condition. Those skilled in the art will appreciate that different wavelengths of light emitted from a luminaire may be suitable to treat various light treatable conditions. For example, in the case of colorblindness, emitting a particular wavelength of light may enable a person who may not be able to view blue colors, for example, to once again view blue colors due to the effect of the wavelength of the light emitted from the luminaire.

Referring now to FIG. 2, a side view of the eye analysis system 2 of the system 25 suitable for treating light treatable conditions and the eye testing module 11 are illustrated. The eye testing module 11 may include an observation optical system 11a and an optical sensor system 11b. The face of a user or patient 12 may rest on the chin rest 13 in a manner so that the eye testing module may be aligned to his eyes.

The optical diagnostic system 11a may include a luminaire integrated into the system that may emit diagnostic output spectra into the eyes of the patient 12. The diagnostic output spectra may have a spectral power distribution configured to generate a biotic response in the eyes of the patient 12. More specifically, the diagnostic output spectra may have a spectral power distribution that, when incident upon the eyes of the patient 12, may generate a biotic response that is indicative of a light-treatable condition. The optical sensor system 11b may measure a biotic response to the diagnostic output spectra. The measured response may define a measured biotic response. The computer 15, which is in communication with each luminaire of 11a and the optical sensor system 11b, may analyze the measured biotic response to determine whether a light-treatable condition is detected. If a light-treatable condition is detected, the computer 15 may further determine an output spectrum or spectra that is responsive to treat a light treatable condition, being defined as a prescribed output spectra. The luminaire of 11a may be configurable to emit the prescribed output spectra by receiving an instruction from the computer 15. More specifically, the luminaire of 11a may include a light source that is operable to emit a light having a spectral power distribution that conforms to the prescribed output spectra. Moreover, the luminaire of 11a may be configured so as to be programmable to operate the light source to emit light having a spectral power distribution conforming to the prescribed output spectra. More information regarding the programming of the luminaire may be found in U.S. patent application Ser. No. 13/751,180, which is incorporated hereinabove.

The measured biotic response may be a retinal response, an eye spectral response and/or a pupillary light reflex. These biotic responses are exemplary only, and any biotic response may also include any optical response of a patient that is detectable by optical sensor system 11b and may be included as a measured biotic response. The pupillary light reflex response may also include pupil size measurements which may measure how the pupil dilates in response to diagnostic output spectra.

In an embodiment of the system 25 according to the present invention, the system may be configured to alleviate light treatable conditions such as color blindness. Color blindness is a deficiency of color vision. There is no actual blindness but there is a deficiency of color vision. The most usual cause is a fault in the development of one or more sets of retinal cones that perceive color in light and transmit that information to the optic nerve. Color blindness can also be produced by physical or chemical damage to the eye, the optic nerve, or parts of the brain. For example, people with achromatopsia suffer from a completely different disorder, but are nevertheless unable to see colors.

If a patient suffers from color blindness, the luminaire of 11a may be programmed to emit light spectra of a wavelength that is discernible by the patient. For example, a patient that suffers from red-green color blindness may receive a luminaire that emits light that would make red or green colors appear to be a different color so that the patient may perceive the existence of multiple colors.

Skilled artisans will recognize that the luminaire of 11a may be configured to emit light spectra of any color as defined by the CIE 1931 XYZ color space. For purposes of definition, the CIE 1931 XYZ color space, created by the International Commission on Illumination, is a red-green-blue (RGB) color space that may be characterized in three dimensions by tristimulus values which represent the luminance and chromaticity of a color (incorporated herein by reference). More information regarding the emission of light spectra of any color may be found in U.S. patent application Ser. No. 13/737,606 titled Tunable Light System and Associated Methods filed Jan. 9, 2013, the content of which is incorporated herein by reference in its entirety.

The prescribed output may be based at least in part on the visual acuity of a patient 12. Visual acuity defines the sharpness of vision and is measured by the ability to discern letters or numbers at a given distance. The optical sensor system 11a may determine the acuity of the patient depending on the responses to certain questions and stimuli in addition to the use of diagnostic output spectra. When the visual acuity of the patient is determined, the luminaire of 11a may be programmed to emit the prescriptive output spectra that alleviate the poor visual acuity experienced by the patient.

The controller or user interface 3 may include a user interface that may be part of the computer 15 and may be configured to receive a patient's light preferences. The controller or user interface 3 may enable the computer 15 to be operated via a keyboard, mouse, pointer, touch screen input system, or any other input device. A user may utilize the controller or user interface 3 to select various operations on the examination system 2.

The computer 15 may also be further configured so that the prescribed output spectra for the patient 12 may be based on the patient's light preferences. The prescribed output spectra may also be based at least in part on a task performed by a patient or the time of day during which the patient will observe the prescribed output spectrum.

A patient's light preferences may include a preference for a particular shade or hue of a color. For example, a user may like colors with a reddish tint. As a result, a luminaire may be programmed for that user that adds more red to its emitted colors by adding light spectra of a particular wavelength into the luminaire's emissions. Furthermore, a user may like light of a particular color temperature. Accordingly, the luminaire may be programmed to emit light having a spectral power distribution that forms a metamer that may be perceived as the preferred color temperature. Similarly, the patient's light preferences may indicate that the patient does not like a particular color or shade of colors. As a result, a luminaire may be programmed to negative the effect or presence of colors not pleasing to the user by removing light spectra of a particular wavelength from the luminaire's emissions.

The patient's tasks may also influence the prescriptive output spectra. For example, tasks requiring a higher CRI or the ability to distinguish between colors that are almost imperceptible by a patient, a luminaire may be programmed to emit prescribed output spectra of a particular wavelength to assist the patient and improve their vision in that regard.

Additionally, the patient's light preferences may indicate a light-treatable condition such as insomnia caused by melatonin suppression. In such examples, the prescribed output spectra may have a spectral power distribution that excludes wavelengths of light associated with melatonin suppression. More information regarding melatonin suppression and its avoidance may be found in U.S. patent application Ser. No. 13/652,207, which is incorporated by reference hereinabove.

In an alternative embodiment, the luminaire may include an autonomous clock so that the luminaire may emit the prescribed output spectra at an indicated time of day. Therefore, if a patient prefers to use a luminaire at a particular time of day, the luminaire may be programmed to automatically emit the prescribed output spectra at that time. As a result, the patient will not have to worry about switching the luminaire on or off when they would typically prefer to utilize the luminaire. In some embodiments, the autonomous clock may be an atomic clock.

Figure 3:
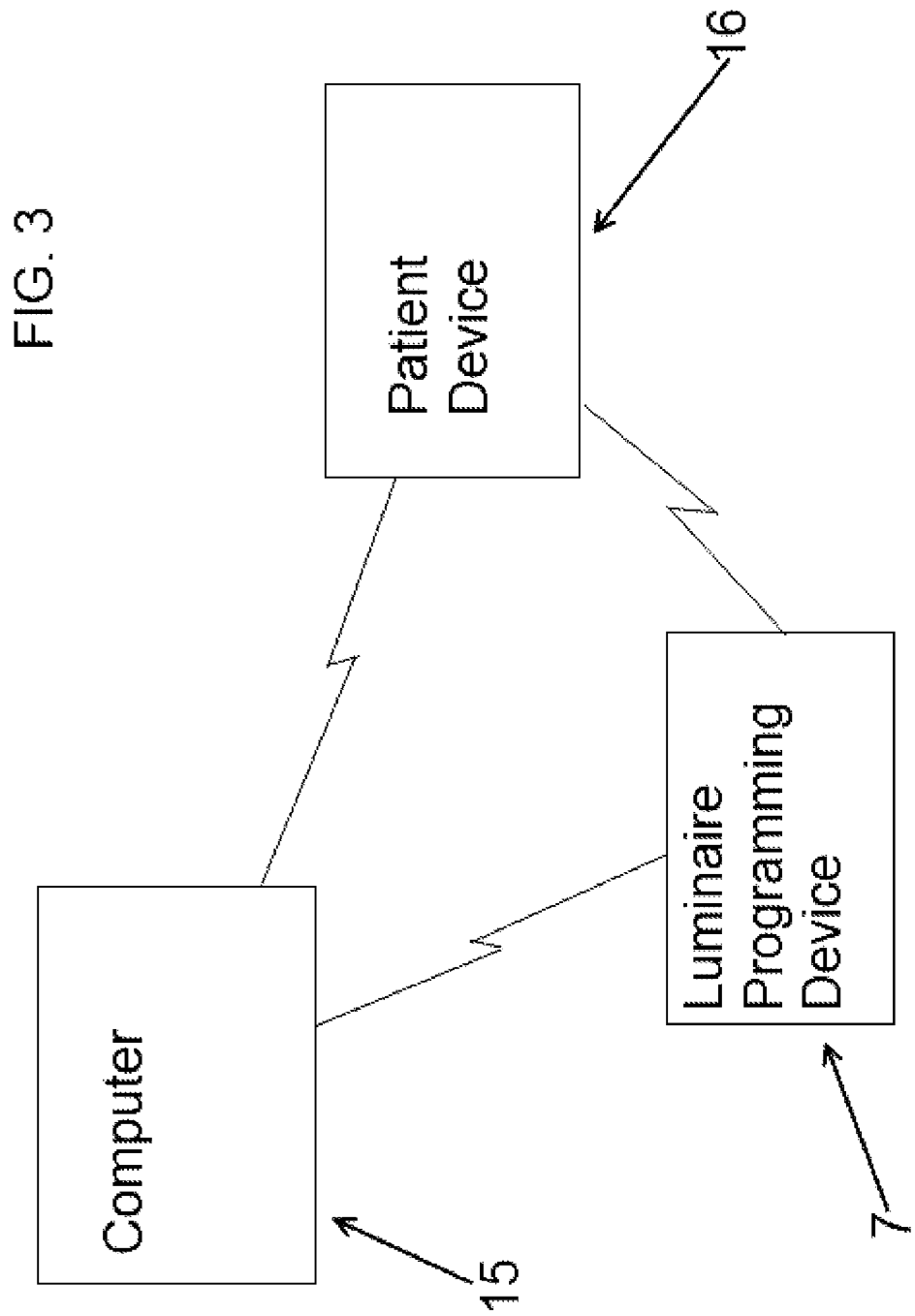
FIG. 3 is a diagram of a computer, luminaire programming station and patient device communicating according to an embodiment of the present invention.

Referring to FIG. 3, the prescribed output spectra as determined by the computer 15 may be transmitted to a patient device 16. The prescribed output spectra may also be transmitted to the luminaire programming station 7. The luminaire programming station 7 may program a second luminaire for use by the patient based upon instructions received from the computer 15. Examples of a luminaire may be include light-emitting semiconductors such as light emitting diodes (LEDs), and any other luminaire known in the art whose spectral distribution may be modified. The luminaire programming station 7 may alternatively receive programming instructions from a patient device 16. A patient device may be another computer, cell phone, smart phone or handheld mobile device such as a PDA or a tablet. In some embodiments, the instructions for the prescribed output spectra may be implemented on a patient device 16. When the prescribed output spectra is implemented on a patient device 16, the color scheme of the patient device 16 may be altered or changed to so that the patient device 16 displays the colors defined by the instructions for the prescriptive output spectra received from the computer 15. In an alternative embodiment, the instructions for prescriptive output spectra may be also implemented on televisions, monitors and projectors (collectively referred to as monitors) so that these monitors may display the colors defined by the instructions for the prescriptive output spectra. Alternatively, where the prescribed output spectra selectively excludes light within a particular wavelength range associated with a color, the prescribed output spectra may be similarly implemented on the monitors so as not to emit light having that color.

In an alternative embodiment, the examination system 2 may also include a network or cloud to which the computer 15 and medical database is connected. The medical database may include medical information that may be utilized to diagnose a medical condition. The luminaire may be configurable to emit a prescribed output spectra responsive to treat the light treatable condition where the computer 15 utilizes the medical database to determine the prescribed output spectra to treat the light treatable condition. The computer 15 may be configured to determine a diagnosis based at least in part on the biotic response to the diagnostic output spectra.

Figure 4:
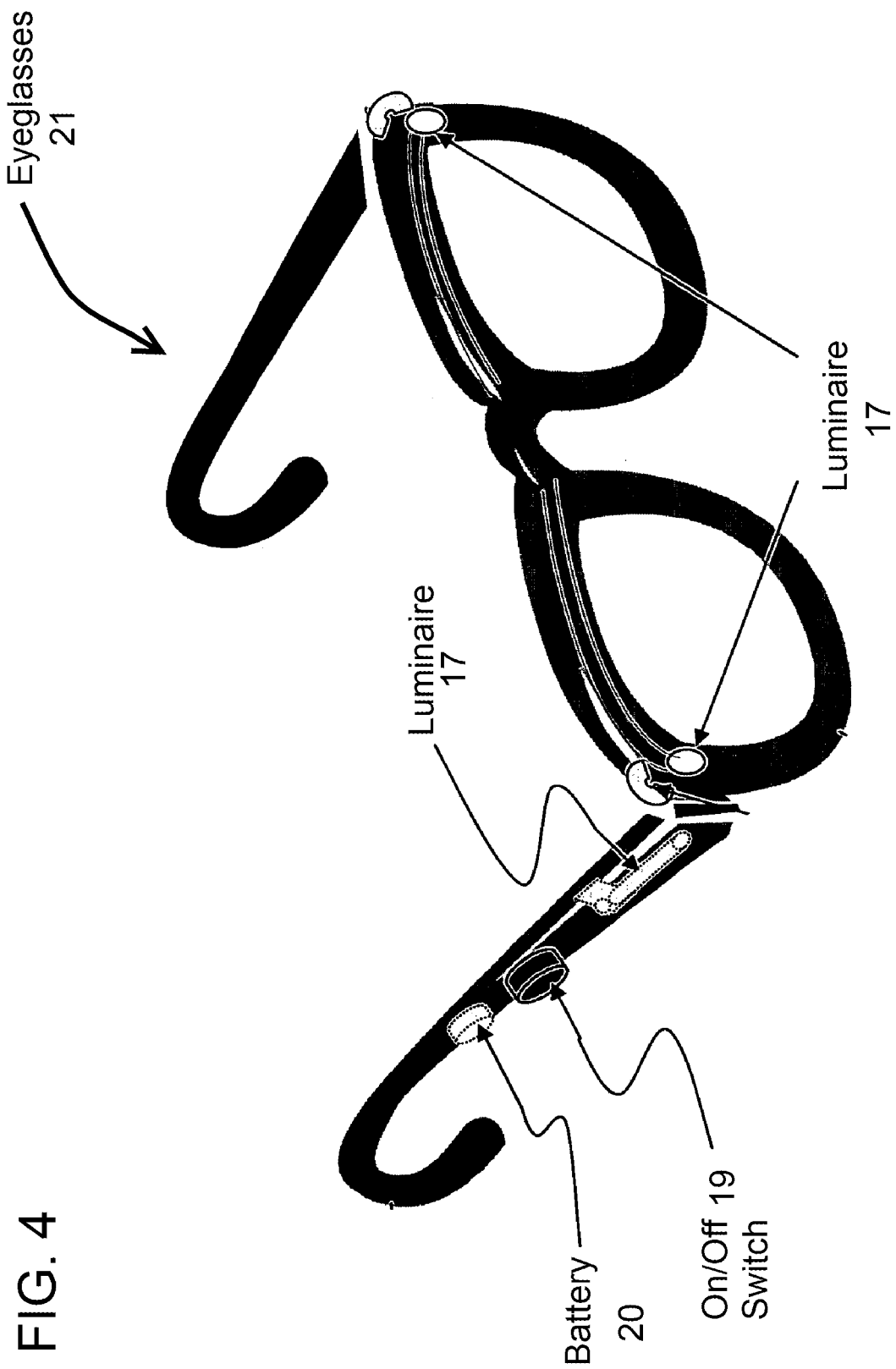
FIG. 4 is a front view of an embodiment of the present invention wherein eyeglasses are equipped with a programmable luminaire suitable for treating a light treatable condition.

Referring to FIG. 4, in another embodiment of the present invention, eyeglasses 21 may be used to emit light to treat the light treatable condition. The eyeglasses 21 may include a battery 20, an on/off switch 19 and a programmable luminaires 17. The on/off switch 19 may be used to turn luminaire 17 on or off. Luminaire 17 may be powered by battery 20. The luminaire 17 may be programmed to emit prescribed output spectra so that a user that is color blind may be able to distinguish the existence of colors that were previously imperceptible.

Figure 5:
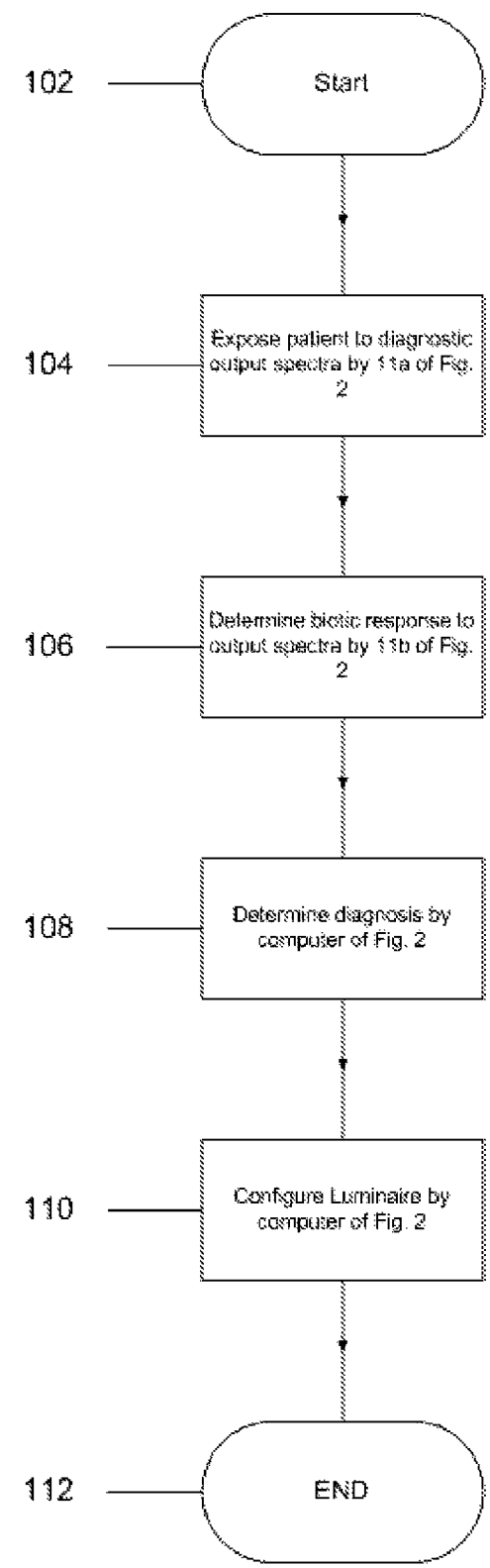
FIG. 5 is a flowchart illustrating a method aspect of the present invention.

Referring now to FIG. 5, in accordance with an embodiment of the invention, a method is illustrated by flowchart 100. Starting at Block 102, the method may proceed to Block 104, where a patient may be exposed to diagnostic output spectra. At Block 106, the patient's biotic response to the output spectra may be determined. At Block 108, the diagnosis for the patient is determined and at Block 110, a luminaire may be configured to emit prescriptive output spectra. The method may end at Block 112.

In a method aspect of the invention, the measured patient's response may include a retinal response, eye spectral response or a pupillary light reflex. The prescribed output spectra may be based upon the visual acuity of the patient.

In a further method aspect of the invention, the computer 15 may be configured to receive information regarding the patient's light preferences via the user interface 3 and also receive those light preferences.

In another method aspect of the invention, the prescribed output spectra may be responsive to a task performed by a patient and/or a time of day during which the patient will observe the prescribed output spectrum. The computer may be further configured to determine prescriptive output spectra responsive to the patient's visual acuity, the patient's biotic response and the patient's light preferences.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed.

What is claimed is:

1. A system for treating a light treatable condition, the system comprising:
    a luminaire configured to emit diagnostic output spectra;
    a sensor configured to measure a biotic response to the diagnostic output spectra to define a measured biotic response; and
    a computer in electrical communication with each of the luminaire and the sensor for utilizing the measured biotic response to determine a prescribed output spectra that is responsive to treat the light treatable condition;
    wherein the luminaire is configurable to emit the prescribed output spectra by receiving an instruction from the computer.

2. A system according to claim 1 wherein the measured biotic response is at least one of retinal response, eye spectral response and pupillary light reflex.

3. A system according to claim 1 wherein the prescribed output spectra is based at least in part on a visual acuity of a patient.

4. A system according to claim 1 wherein the computer further comprises a user interface configured to receive a patient's light preferences.

5. A system according to claim 4 wherein the computer is further configured so that the prescribed output spectra for the patient is based on at least one of a visual acuity of the patient, the measured biotic response, and the patient's light preferences.

6. A system according to claim 5 wherein the prescribed output spectra is transmittable to a patient device.

7. A system according to claim 1 wherein a second luminaire is configurable to emit the prescribed output spectra based on receipt of instructions from the computer.

8. A system according to claim 1 wherein the prescribed output spectra is responsive to at least one of a task performed by a patient and a time of day during which the patient will observe the prescribed output spectrum.

9. A system according to claim 8 wherein the prescribed output spectra is responsive to the time of day during which the patient will observe the prescribed output spectra; and wherein the luminaire comprises an autonomous clock configured to cause the luminaire to emit the prescribed output spectra at an indicated time of day.

10. A system for treating a light treatable condition, the system comprising:
    a luminaire configured to emit diagnostic output spectra;
    a sensor configured to measure a biotic response to the diagnostic output spectra;
    a computer in electrical communication with each of the luminaire and the sensor and being connected to a network;
    a medical database connected to the network comprising medical information related to a diagnosis of medical conditions; and
    a luminaire that is configurable to emit a prescribed output spectra;
    wherein the computer utilizes the medical database to determine the prescribed output spectra responsive to treat the light treatable condition;
    wherein the computer is configured to determine a diagnosis based at least in part on the biotic response to the diagnostic output spectra that is responsive to the diagnosis.

11. A system according to claim 10 wherein a second luminaire is configured to emit the prescribed output spectra.

12. A method for treating a condition in a patient having a light treatable condition, the method comprising:
- exposing the patient to diagnostic output spectra;
- determining the patient's response to the diagnostic output spectra to define a measured patient's response;
- determining a diagnosis of the patient based, at least in part, on the patient's response to the diagnostic output spectra;
- determining a prescribed output spectra that is responsive to the diagnosis; and
- configuring a luminaire to emit the prescribed output spectra.

13. A method according to claim 12 wherein the measured patient's response is at least one of retinal response, eye spectral response and pupillary light reflex.

14. A method according to claim 12 wherein the prescribed output spectra is based at least in part on a visual acuity of the patient.

15. A method according to claim 12 wherein the luminaire is configurable to emit the prescribed output spectra by receiving an instruction from a computer.

16. A method according to claim 15 wherein the measured patient's response is at least one of the patient's retinal response, the patient's eye spectral response and the patient's pupillary light reflex.

17. A method according to claim 16 wherein the computer is configured to receive information regarding the patient's light preferences via a user interface; and further comprising receiving a patient's light preference.

18. A method according to claim 17 wherein the prescribed output spectrum is responsive to at least one of a task performed by a patient and a time of day during which the patient will observe the prescribed output spectrum.

19. A method according to claim 18 wherein the computer is further configured to determine prescriptive output spectra for the patient responsive to at least one of a visual acuity of the patient, the measured biotic response, and the patient's light preferences.

20. A method according to claim 19 further comprising the step of transmitting the prescribed output spectrum to a patient device.

* * * * *